United States Patent [19]

Szybalski

[11] Patent Number: 4,935,357

[45] Date of Patent: Jun. 19, 1990

[54] UNIVERSAL RESTRICTION ENDONUCLEASE

[75] Inventor: Waclaw Szybalski, Madison, Wis.

[73] Assignee: New England Biolabs, Inc., Beverly, Mass.

[21] Appl. No.: 826,220

[22] Filed: Feb. 5, 1986

[51] Int. Cl.$^5$ .......................... C12P 19/34; C12N 9/22
[52] U.S. Cl. ...................................... 435/91; 435/199; 935/19
[58] Field of Search .......................... 435/91, 199, 6, 7; 935/19

[56] References Cited

U.S. PATENT DOCUMENTS

| 4,581,333 | 4/1986 | Kourilsky et al. | 435/6 |
| 4,670,379 | 6/1987 | Miller | 435/6 |

OTHER PUBLICATIONS

Maniakis, T. et al., Moleendar Cloning, A Laboratory Manual, Cold Spring Harbor Laboratory, 1982, pp. 392–393.

Primary Examiner—Thomas G. Wiseman
Assistant Examiner—Charles L. Patterson, Jr.
Attorney, Agent, or Firm—Gregory D. Williams; David G. Conlin; Patricia A. McDaniels

[57] ABSTRACT

A universal restriction endonuclease for cleaving a target DNA at a predetermined site. The universal restriction endonuclease utilizes a tailored oligodeoxynucleotide adapter in conjunction with a restriction enzyme which cuts DNA at a known distance from its recognition site. The oligodeoxynucleotide adapter mimics the relationship which exists in such enzymes between its recognition site and cut site.

12 Claims, 7 Drawing Sheets

UNIVERSAL RESTRICTION ENDONUCLEASE

Background of the invention

The present invention relates to novel universal restriction endonucleases and to methods of producing such endonucleases. More specifically, the present invention relates to restriction endonucleases which allow one to cleave practically any predetermined DNA sequence by combining an oligodeoxynucleotide adapter with a known restriction endonuclease.

Restriction endonucleases are a class of enzymes that occur naturally in bacteria. When they are purified away from other interfering bacterial components, restriction endonucleases can be used in the laboratory to cut DNA molecules into precise fragments. This property enables DNA molecules to be uniquely identified and to be precisely fractionated into their constituent subunits. Restriction endonucleases have proved to be indispensable tools in modern genetic research. They are the biochemical 'scissors' by means of which genetic engineering and analysis is performed.

Restriction endonucleases are classified into three groups. Class-I and Class-III enzymes carry modification (methylation) and an ATP-requiring restriction (cleavage) activity in the same protein moiety. Both types of enzymes recognize unmethylated recognition sequences in substrate DNA, but Class-I enzymes cleave largely randomly, whereas Class-III enzymes cut DNA at specific sites, generally at a constant distance from their recognition sites.

Class-II restriction/modification system consist of a separate restriction endonuclease and modification methylase. These enzymes cut DNA within or near their particular recognition sequences, which typically are four to six nucleotides in length, frequently with a twofold axis of symmetry. There exist more than 500 Class II restriction endonucleases that cleave DNA at specific sites. The number of different recognition sites is greater than 100 (not counting various modifications, including methylation) (Roberts, Nucl. Acids Res., 13:r165, 1985; Kessler et al. Gene, 33:1-102, 1985). Although the existing repertoire of cleavage sites is of great value, there is frequently a need for additional cut sites to permit precise engineering of genes and regulatory sequences. At present, to access a sequence where a favorable restriction site is not available, one usually engineers the sequence by a variety of methods, including insertion of appropriate linkers, mutagenesis, or exonucleolytic digestion. However, such methods for creating a new site modify the nucleotide sequence under study and may often affect its function.

SUMMARY OF THE INVENTION

In accordance with the present invention, there is provided a novel approach to the engineering of restriction enzymes which can cleave DNA at a specific predetermined site. In one embodiment Class IIS or "shifter" enzymes are utilized. Class IIS enzymes are defined as those Class II endonucleases which cleave double-stranded (ds) DNA at precise distances from recognition sequences. Certain Class III enzymes may also be used in practicing the present invention, particularly those which cut at a reasonably constant distance (at about 20-25 nucleotides) from their recognition site. Class II enzymes with cut sites between two recognition sites (e.g., BstXI enzyme; see Gene 40:173 (1985)) may also be used in accordance with the teachings of the present invention.

The present invention utilizes the separation between the recognition site and the cut site to allow Class II or Class III enzymes to cleave practically any predetermined sequence by combining the enzyme with a properly designed oligodeoxynucleotide adapter. The adapter is constructed from the constant recognition site domain (a hairpin-containing ds sequence) and a variable, single-stranded (ss) domain complementary to the target ss sequence to be cleaved. The ss sequence to be cleaved may be provided by ss phage DNA, gapped ds plasmids, supercoiled ds plasmids that are alkali denatured and rapidly neutralized, or the like. Combination of these three components, i.e., the Class IIS enzyme, the ss DNA target sequence, and the complementing adapter, result in a novel restriction-endonuclease complex which cleaves the target DNA at a specific predetermined site. A further advantage of the present invention is that the target ss DNA may be converted to the precisely cleaved ds DNA by an appropriate DNA polymerase, utilizing the adapter oligodeoxynucleotide as a primer.

Thus, in accordance with the present invention, there is provided a method of changing the enzyme specificity of restriction endonucleases by synthetic design leading to a practically unlimited assortment of new endonucleases having predetermined restriction specificities.

DETAILED DESCRIPTION OF THE INVENTION

The present invention provides purposefully designed oligodeoxynucleotide adapters which can be used to modify the specificity of restriction endonucleases. The adapters instruct these enzymes to cleave DNA at a predesignated target site. In other words, the oligodeoxynucleotide adapters, which may be likened to novel synthetic "coenzymes", confer a new substrate specificity upon a restriction endonuclease.

The oligodeoxynucleotide adapters of the present invention are used to mimic the relationship which exists in certain restriction endonucleases between their recognition sites and cut sites so as to provide the modified endonuclease with the ability to cut DNA at practically any predetermined site on a target DNA. Preferred restriction enzymes, modified in accordance with the present invention, are class IIS enzymes for which the cleavage site is shifted a considerable (up to 13 nucleotides), but precise, distance from the recognition site. The recognition sites and displacements of cleavage sites of 11 Class IIS restriction enzymes are listed in Table I. In accordance with the present invention, such oligodeoxynucleotide adapter molecules to instruct the enzyme to recognize and cut any predetermined DNA sequence. As noted above, Class III enzymes, preferably those which cut at about 20-25 nucleotides from their recognition site, and other Class II enzymes, e.g., BstXI, may also be modified to function as a universal restriction endonuclease by the use of analagous adapters in accordance with the teachings of the present invention. Such enzymes include EcoPl, EcoP15, and HinfIII; see Kessler et al., supra, pp.67-68.

TABLE I

Properties of class IIS restriction endonucleases ("shifters")

| Enzyme | recognition sequence[a] | | Protruding end[b] | Reference[c] Page | Entry |
|---|---|---|---|---|---|
| BbvI[d,e] | 5'-GCAGCN$_8$ ↓<br>CGTCGN$_{12}$ ↓ | 5'- ↓ N$_{12}$GCTGC<br>↓ N$_8$CGACG | 5'N$_4$ | 57 | 513 |
| BbvII | 5'-GAAGACN$_2$<br>CTTCTGN$_6$ | 5'-N$_6$GTCTTC<br>N$_2$CAGAAG | 5'N$_4$ | 102 | — |
| BinI | 5'-GGATCN$_4$<br>CCTAGN$_5$ | 5'-N$_5$GATCC<br>N$_4$CTAGG | 5'N$_1$ | 57 | 516 |
| FokI[d,e] | 5'-GGATGN$_9$<br>CCTACN$_{13}$ | 5'-N$_{13}$CATCC<br>N$_9$GTAGG | 5'N$_4$ | 57 | 519 |
| HgaI[d,f] | 5'-GACGCN$_5$<br>CTGCGN$_{10}$ | 5'-N$_{10}$GCGTC<br>N$_5$CGCAG | 5'N$_5$ | 58 | 526 |
| HphI[d,e] | 5'-GGTGAN$_8$<br>CCACTN$_7$ | 5'-N$_7$TCAGG<br>N$_8$AGTCC | 3'N$_1$ | 58 | 527 |
| MboII[d,e] | 5'-GAAGAN$_8$<br>CTTCN$_7$ | 5'-N$_7$TCTTC<br>N$_8$AGAAG | 3'N$_1$ | 58 | 528 |
| MnlI[d,f] | 5'-CCTCN$_7$<br>GGAGN$_7$ | 5'-N$_7$GAGG<br>N$_7$CTCC | blunt | 59 | 531 |
| SfaNI[d,f] | 5'-GCATCN$_5$<br>CTGAGN$_9$ | 5'-N$_9$GATGC<br>N$_5$CTACG | 5'N$_4$ | 59 | 532 |
| TaqII |     G   G<br>5'-CACCCAN$_{11}$<br>CTGGCTN$_9$<br>    G   G |         G   G<br>5'-N$_9$ TCGGTC<br>N$_{11}$ACCCAC<br>        G   G | 3'N$_2$ | 59 | 533 |
| Tth111II[g] | 5'CAAPuCAN$_{11}$<br>GTTPyGTN$_9$ | 5'N$_9$ TGPyTTG<br>N$_{11}$ACPuAAC | 3'N$_2$ | 59 | 535 |

[a] Since the recognition sites are not palindromic, both orientations are listed. Arrows specify the cleavage sites shown only for the first enzyme.
[b] The 5' or 3' protruding ss ends of the restriction sites are indicated and their lengths given.
[c] Refers to the review of Kessler et al., (supra), with the page and entry number specified.
[d] Commercially available (e.g., New England Biolabs; see Kessler et al., supra).
[e] No endonucleolytic activity toward M13 ss DNA.
[f] The tested batch of the enzyme displayed an endonucleolytic activity toward M13 ss DNA. However, the enzymes may be purified to remove the endonucleotic activity.
[g] Py = T or C; Pu = A or G. For cut points see Roberts, supra.

Class IIS enzymes may be engineered by using synthetic

TABLE I-continued

Properties of class IIS restriction endonucleases ("shifters")

| Enzyme | recognition sequence[a] | | Protruding end[b] | Reference[c] Page | Entry |
|---|---|---|---|---|---|
| MnlI[d,f] | CTTCN$_7$<br>5'-CCTCN$_7$<br>GGAGN$_7$ | N$_8$AGAAG<br>5'-N$_7$GAGG<br>N$_7$CTCC | blunt | 59 | 531 |
| SfaNI[d,f] | 5'-GCATCN$_5$<br>CTGAGN$_9$ | 5'-N$_9$GATCG<br>N$_5$CTACG | 5'N$_4$ | 59 | 532 |
| TaqII | G  G<br>5'-CACCCAN$_{11}$<br>CTGGCTN$_9$ | G  G<br>5'-N$_9$ TCGGTC<br>N$_{11}$ACCCAC | 3'N$_2$ | 59 | 533 |
| TthlllI[g] | G  G<br>5'CAAPuCAN$_{11}$<br>GTTPyGTN$_9$ | G  G<br>5'N$_9$ TGPyTTG<br>N$_{11}$ACPuAAC | 3'N$_2$ | 59 | 535 |

[a]Since the recognition sites are not palindromic, both orientations are listed. Arrows specify the cleavage sites shown only for the first enzyme.
[b]The 5' or 3' protruding ss ends of the restriction sites are indicated and their lengths given.
[c]Refers to the review of Kessler et al., (supra), with the page and entry number specified.
[d]Commercially available (e.g., New England Biolabs; see Kessler et al., supra).
[e]No endonucleolytic activity toward M13 ss DNA.
[f]The tested batch of the enzyme displayed an endonucleolytic activity toward M13 ss DNA. However, the enzymes may be purified to remove the endonucleotic activity.
[g]Py = T or C; Pu = A or G. For cut points see Roberts, supra.

Figure 1:
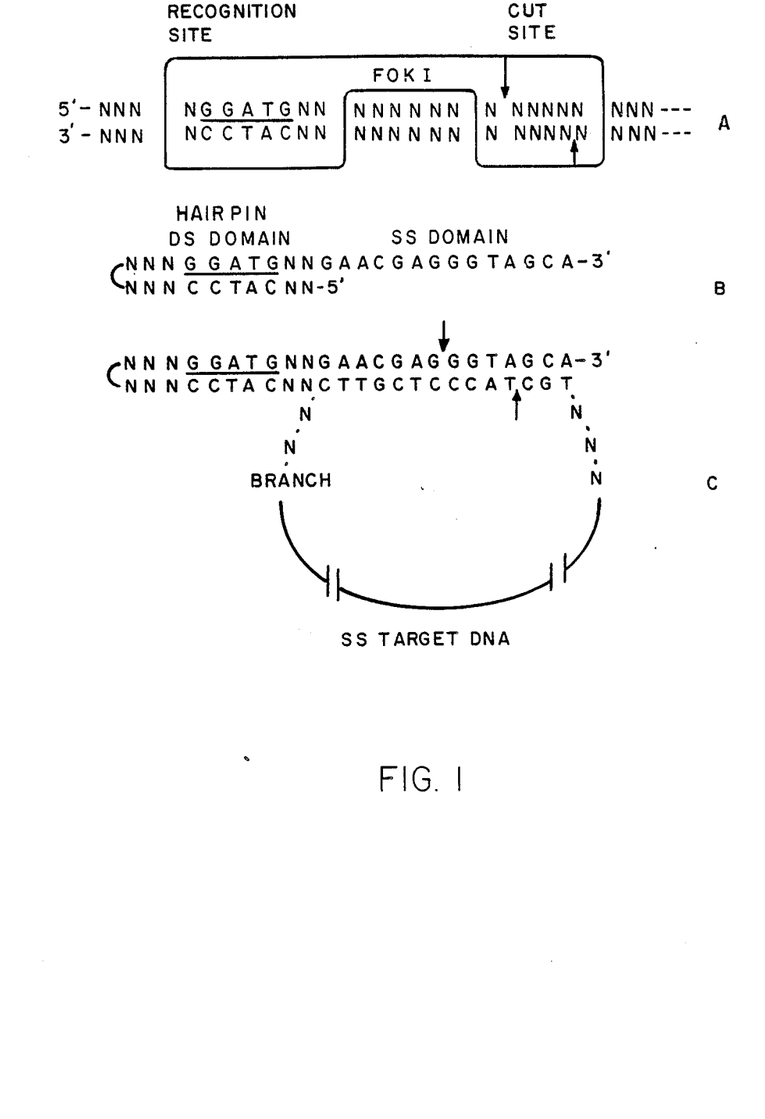
FIG. 1 illustrates the design scheme of an oligodeoxynucleotide adapter for instructing the FokI Class IIS enzyme to cleave M13 ss DNA at a predetermined point.

Referring now to FIG. 1, there is shown the outline of the principle of the present invention as applied to the FokI endonuclease. The relationship between the FokI recognition site, GGATG, CCTAC, and the staggered sites on the normal ds DNA molecule are shown in FIG. 1a. The adapter oligodeoxynucleotide (FIG. 1b) that mimics the above arrangement consists of the hairpin ds domain, which carries the recognition sequence (underlined), and an ss domain where the cleavage(s) would occur after pairing with the complementary target DNA strand. Thus, the ds domain of the adapter is a constant part that provides the specificity of the Class II enzyme, whereas the ss domain is a variable and can be designed in accordance with the present invention to provide cleavage at any chosen site in the complementary target DNA.

DESIGN OF THE ADAPTER

The oligodeoxynucleotide depicted in FIG. 1b will serve as an example of adapter design for the Class II FokI enzyme and ss target DNA from the M13 phage. The hairpin ds domain of the 34-mer contains the 5'-GGATG recognition site for FokI; its ss domain 3'-CCTAC was designed to direct the cleavage between T and C in the target M13 DNA. The complex between the adapter and M13 DNA (FIG. 1c) mimics a ds module (FIG. 1a) which contains both the FokI recognition site and the ds cleavage site (see Table I and FIG. 1c). Depending on the sequence of the ss domain of the adapter, the enzyme would cut at any chosen site on the target DNA. At the same time, the 3' end of the adapter (see FIG. 1b,c) could serve as primer for synthesis of the strand complementary to the target ss DNA, either in one stage using all four dNTPs, or in two stages: a limited synthesis with three dNTP's (to anchor the 3' end of the adapter before FokI digestion, but not so extensive as to provide ds recognition sites for FokI), followed by synthesis of the total complementary strand after the FokI cleavage.

FIG. 1 does not indicate optimal adapter design. Optimization includes: (i) determination of the most efficient hairpin lengths to the left and to the right of the GGATG recognition site; (ii) alteration of the length of the ss domain complementary to the cleaved ss DNA and/or to provide the primer function; (iii) modification of the position of the ss M13 DNA branch (FIG. 1b) with respect to the GGATG and cleavage sites; (iv) comparison of adapters with the 5' and 3' ss domains (see FIG. 2); (v) possible use of ambiguous nucleotides (inosinic acid) or ribonucleotides in the ss domain of the adapter; and (vi) inclusion of reactive deoxynucleotides (e g , 5-iododeoxyuridine nucleotides) in the tip of the hairpin in order to form covalent (but active) adapter-enzyme complexes upon light UV irradiation. Other methods of adapter-enzyme complexing could also be used. Optimization of adapter design also facilitates a better understanding of the mechanism of the endonucleolytic activity of restriction endonucleases.

Figure 2:
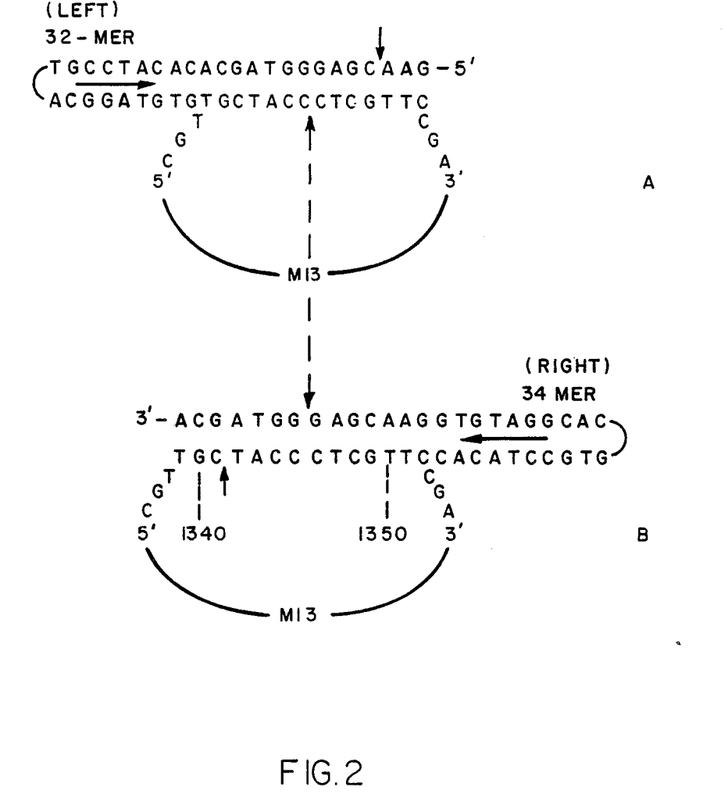
FIG. 2 illustrates two oligodeoxynucleotide adapters for use with the restriction endonuclease.

Although it is necessary to design a specific adapter for each chosen cleavage site, only the variable ss domain (5–15 nucleotides) has to be custom-made. It could then be either (i) ligated to the stem of the constant ds hairpin domain, using as a splicing support a set of oligodeoxynucleotides designed to be complementary to the adjoining sequences of the hairpin and ss domains or, (ii) prepared by first synthesizing a supply of the constant hairpin domain with protective groups retained, and in the second synthetic stage adding the variable ss domain. Such two-step organic synthesis is possible for adapters containing the 5' ss domain (see FIG. 2a), because of the 3'to 5' direction of the nucleotide coupling.

Although adapter synthesis must be customized for many sequences, in accordance with the present invention, an inventory of adapters for large numbers of commonly encountered sequences for which no enzymes are presently available may be prepared.

TARGET DNA AND VECTORS (1) Single-stranded DNA

One of the main advantages of using ss target-vector DNA, as exemplified by M13 ss DNA shown in FIG. 1, is that it does not provide recognition sites for most of the Class IIS enzymes, which are rather frequent cutters of ds vectors. Several commercially available Class IIS enzymes (FokI, HphI, MboI, BbvI; New England Biolabs) do not have interfering endonucleolytic activity toward M13 DNA. The ss target DNA could be obtained from a variety of sources, including the ss DNA phage vectors (M13, fd, f1) or any ds plasmid carrying the replication origin (ori) of those phages that convert ds plasmids to packaged ss DNA upon phage superinfection.

(2) Double-stranded DNA with ss gaps

Another substrate could be ds DNA with properly designed ss gaps, but in this case the ds cleavage sites should preferably be either absent or rendered inactive by (i) methylation or other modification of the ds DNA, or (ii) saturation of enzyme with the adapter and possible covalent binding.For the specific methylation of FokI sites, a FokI methylase is available (New England Biolabs). For class IIS enzymes which create 4-nucleotide cohesive ends, the religation of the cleaved plasmid would restore its original arrangement, since each cleavage sequence is unique. However, a cut in the ss gap would remain open, if the uncut adapter were removed. If the purpose of the adapter-mediated cleavage is to produce a small fragment with a specific terminus, the additional FokI cuts in the ds DNA might be of no importance or even beneficial.

(3) Double-stranded DNA

In addition to the problems specified above, use of a ds DNA substrate requires a special method for threading the ss domain of the adapter into the ds target sequence. This should be possible when using reversibly denatured target DNA obtained by alkali denaturation of the supercoiled plasmid DNA followed by rapid neutralization. Such a procedure results in largely denatured molecules shown to anneal with primer oligonucleotides (Chen and Seeburg, DNA 4:165–170, 1985). Use of a single adapter would result in an ss nick, whereas two adapters with barely overlapping or neighboring ss domains complementary to opposing strands would provide staggered cuts. Alternatively, this might be accomplished by use of catalysts, e.g., RecA-like protein, mild denaturation conditions, or of ribonucleotides in the ss domain of the adapter. Also, advantageously, with the adapter shown in FIGS. 1 or 2b, the ds DNA may be obtained by using the 3'-OH end of the adapter as a primer to synthesize the complementary strand, as discussed above.

The present invention permits construction of novel cleavage specificities by combining carefully contrived synthetic adapter molecules with Class IIS or Class III restriction endonucleases. Devising unlimited numbers of new enzymatic specificities ("new restriction enzymes") in accordance with the present invention is limited mainly by oligodeoxynucleotide synthesizer capacity.

Although the present invention is primarily directed to Class IIS restriction endonucleases, it is also possible, in accordance with the teachings herein, to design adapters for enzymes that recognize an inverted repeat separated by a run of nonspecific base pairs. For instance, the adapter

NCCANNNNNTGGN

NGGT    ACCN should convert the enzyme (see Kessler et al., supra) to an endonuclease seeking an ss sequence complementary to the central NNNNNN ss domain of the adapter. Many other kinds of adapters could also be designed.

The following examples are given to additionally illustrate embodiments of the present invention as it is presently preferred to practice. It should be understood that these examples are illustrative, and that the invention is not to be considered as restricted thereto except as indicated in the appended claims.

EXAMPLE 1

Example I describes methods designed to select target DNA, target sequence, restriction enzyme, as well as methods to detect cleavage processes.

(a) Selection of the target DNA: For the purposes of this example, a phage M13 derivative was selected as the source of ss DNA because (i) its entire nucleotide sequence is known (Van Wezenbeek et al., Gene 11:129–148 1980; Yanish-Perron et al., Gene 33: 103–119 1985), (ii) M13mp phages are convenient cloning vectors, and (iii) it is easy to propagate both the ds replicative form (RF) and ss DNA. Among M13 derivatives, the M13mp7 vector phage was selected because its ss DNA contains a small hairpin structure which was designed to be cleaved by enzymes EcoRI, BamHI, HindIII, AccI and SalI (Messing, Methods in Enzymol. 101:20–78, 1983). These cuts provided reference points for confirmatory mapping of the ss cuts by the FokI-adapter complexes, as depicted in FIG. 3.

Figure 3:
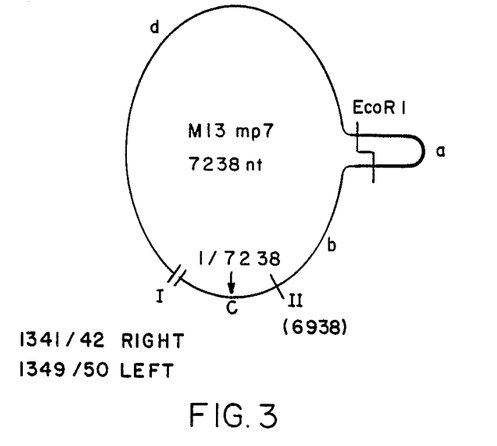
FIG. 3 shows a schematic representation of the M13mp7 ss DNA.

The heavy lines of FIG. 3 represent the ss DNA. The sequence of the hairpin "a" is as follows:

```
      EcoRI         BamHI      SalI
   C
    ⟶GAATTCCCCGGATCCGTCGACCTG
    ⟶CTTAAGGGGCCTAGGCAGCTGGAC⟵
   A
```

Two cuts at position I (FIG. 3) are as described in FIG. 2. The location of cut(s) at position II was found to be located near nucleotide 6938. The length of the entire M13mp17 is 7238 nucleotides, and the approximate lengths of the fragments are: a, 32; b, 670; c, 1640; d, 4890; b+c, 2300; a+b+d, 5600 nucleotides. The drawing is not to scale.

(b) Selection of the target sequences: Using the computer program of the University of Wisconsin Genetics Computer Group on a DESCS VAX 7800 (Devereux et al., Nucleic Acids Res. 12:387–375 1984), a 14-nucleotide sequence in M13mp7 ss DNA was found which satisfied the following criteria: (i) it is unique, (ii) no similar sequences with one, two or three mismatches are present in the phage DNA, (iii) no complementary sequences with 0–2 mismatches are present in the phage, and (iv) the cuts in the selected sequence and at the reference EcoRI site (see cuts I and EcoRI in FIG. 3) would produce two fragments easy to distinguish and measure on gels (ignoring the 32-nucleotide hairpin fragment cut-off by EcoRI). A 14-nucleotide unique sequence 5'-TGCTACCCTCGTTC-3' was selected (nucleotides 1339–1352), with no 0–3 nucleotide mismatches found in M13mp7 ss DNA, with only three 4-nucleotide scattered mismatches (starting at nucleotide 1749, 2908 and 5599), and no 0–2 nucleotide-mismatch-complementary sequences, which might have interfered with the adapter pairing. The sole 3-nucleotide mismatch complementary sequence starts at nucleotide 5443.

Figure 4:
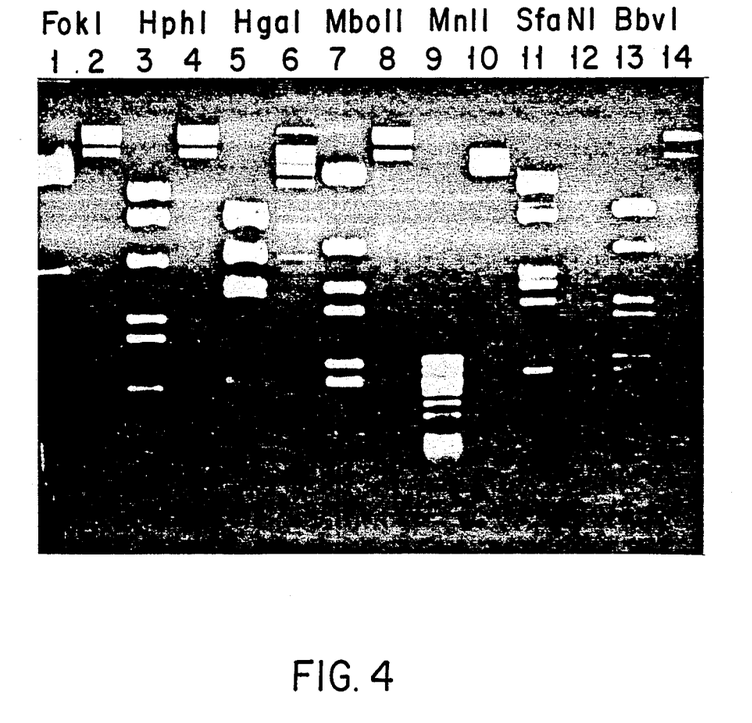
FIG. 4 shows reproduction of photographs of gel digests of ds and ss M13mp7 DNA by FokI, HphI, HpaI, MboII, MnlI, SfaNI and BbvI.

(c) Selection of the restriction enzyme: Testing of all the commercially available Class IIS enzymes revealed that four of them (FokI, HphI, MboII and BbvI) do not show endonucleolytic activity toward ss M13mp7 (FIG. 4). FIG. 4 illustrates cleavage of the replicative form RF ds (lanes 1,3,5,7,9,11,13) and ss (lanes 2,4,6,8,10,12,14) M13mp7 DNA by FokI (8 u; lane 1,2), (8 u; lanes 3,4), HpaI (2 u; lanes 5,6) MboII (20 u; lanes 7,8), MnlI (2 u; lanes 9,10), SfaNI (2 u; lanes 11,12) and BbvI (2 u; lanes 13,14). All enzymes were a gift from New England Biolabs and digestions were carried out for 3 hours at 37° C. under conditions suggested by the manufacturer for the ds DNA, using the indicated number of enzyme units (u; see above in parentheses) per 20 ul of digestion mix per 2 ug DNA. Conditions of sample preparation and electrophoresis of ss M13mp7 DNA were the same as described below in connection with FIG. 6. Conditions for sample preparation with digestion of ds DNAs were as in Maniatis et al. (1982). DNA was stained with ethidium bromide and photographed using UV light trans-illumination. For the first phase was selected because of previous experience with this enzyme and because a methylase has become commercially available, permitting protection of ds DNA from FokI digestion at preexisting restriction sites.

As seen in FIG. 4, Class IIS enzymes HgaI and MnlI show multiple cuts on M13mp7 ss DNA, whereas SfaNI seems to contain some nonspecific endonucleolytic activity toward ss DNA. All seven enzymes show the predicted ds cuts, with the exception of MboII, where Dam methylation interferes with a few cuts (see also Kessler et al., supra).

(d) Design of the adapters: Since the FokI recognition sequence

GGATG

CCTAC is asymmetric, two different oligodeoxynucleotide adapters, "left" (32 nucleotides) and "right" (34 nucleotides), were constructed, as shown and explained in FIG. 2. They were expected to direct two different cuts, 8 nucleotides apart, on the M13mp7 target ss DNA (FIGS. 2 and 3). The adapter is composed of two domains (see FIG. 1): (i) the constant ds (hairpin) domain which contains the FokI-recognition ds site, and (ii) the variable ss domain complementary to the target sequence described in section b above. The left adapter, with the hairpin ds domain at its 3' end, permits its two-stage synthesis: (i) first, the 3'- to 5'- organic synthesis of a large supply of the constant ds domain in the protected form, and (ii) subsequent addition of several predesigned ss domains complementary to the selected target sequence. The right adapter, with the hairpin ds domain at its 5' end, permits the use of its 3' end as the primer for synthesis of the entire complementary strand of M13mp7 DNA.

Figure 5A:
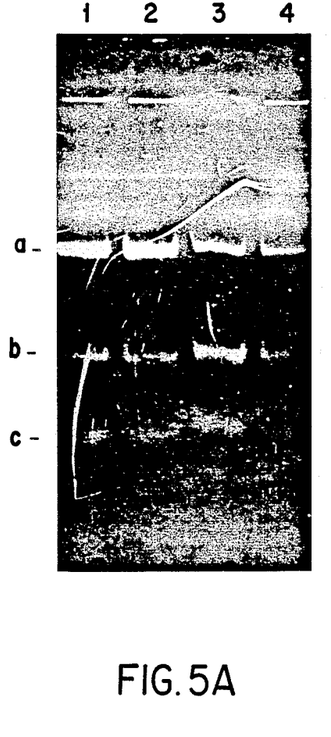
FIG. 5 illustrates conformation of an oligodeoxynucleotide adapter and its insusceptibility to FokI cleavage.
Figure 5B:
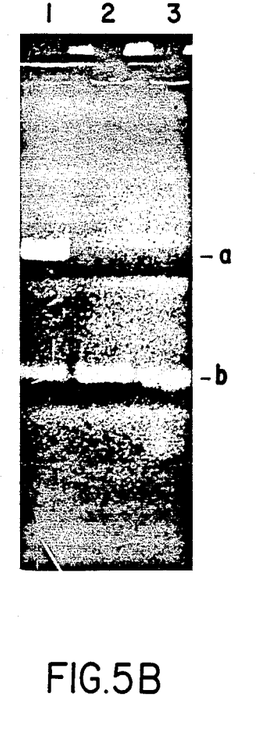

(e) Conformation of the adapters: As seen in FIG. 5, the adapter could exist as a hairpin monomer (see FIG. 2) or form a dimer, as e.g, that corresponding to the right adapter:

5'-CACATCCGTGCACGGATGTGGAAC-
GAGGGTAGCA-3'
3'ACGATGGGAGCAAGGTGTAGGCACGTGC-
CTACAC-5' with the central 20-base pair palindrome susceptible to several restriction enzymes, including and Bsp1286. When electrophoresis was carried out under nondenaturing conditions FIG. 5, A-lane 1 and B-lane 1) the dimers were observed. When the alkaline sample mix or 70° C. treatment in the loading buffer were employed, the dimer bands disappeared (FIG. 5B, lanes 3 and 2, respectively). In the FokI buffer the 34-mer denaturation at 70° C. was partially reversed (FIG. 5A, lane 3). Both monomer and dimer should be active as adapters.

(f) Sensitivity of the adapters to the FokI enzyme: Since it was desired that the FokI enzyme cut only the duplex formed by annealing between the M13 target sequence and the adapter, it was necessary to demonstrate that the enzyme would not cleave the ss domain of the adapter in the absence of complementary DNA strand. FIG. 5 illustrates conformation of the adapter and its insusceptibility to FokI cleavage.

In FIG. 5a, all lanes contain 1 g of 34-nucleotide adapter suspended in buffer (see FIG. 6) and heated for 5 min at 70° C. (lanes 3–4) or thermally untreated (lanes 1–2). Adapter in lanes 2 and 4 was treated with FokI, as described in connection with FIG. 6. Electrophoresis was performed on 20% PA gel in presence of Peacock buffer (Maniatis et al., 1982) at 200 volts, for 5 h. Each well was filled in with 20ul of adapter solution and 5 ul of loading buffer containing bromphenol blue (Maniatis et al., 1982).

In FIG. 5b, all lanes contain 2 ug of 32-nucleotide adapter suspended either in 20 ul of loading buffer (10% glycerol, 7% sucrose, 2.4% Ficol; free of bromphenol blue)—lanes 1 and 2; or in 20 ul of alkaline loading buffer—lane 3. Samples in lane 2 were heated 5 min at 70° C. Samples (20ul) were electrophoresed as in panel A. Bands were stained with ethidium bromide and photographed as in FIG. 4. (a) dimer, (b) monomer, (c) bromphenol blue indicator. This proved to be the case as shown in FIG. 5A (lanes 2 and 4), since adapter alone is not cleaved by FokI. As mentioned in section (d) above, the dimerization of the adapter molecules was observed.

Figure 6:
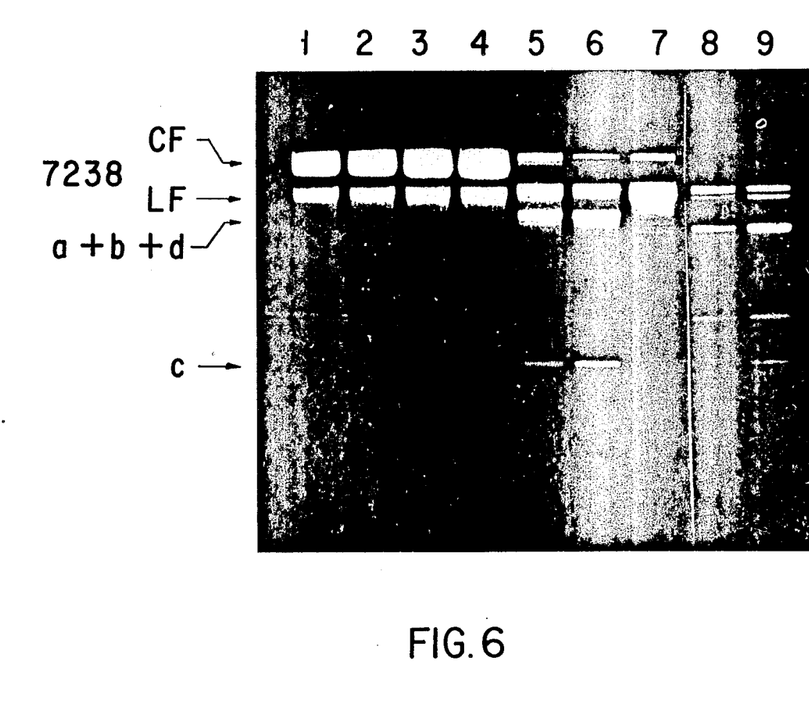
FIG. 6 illustrates photographs of gels of FokI digestion of M13mp7 in the presence of the 32-mer and 34-mer adapters illustrated in FIG. 2.

(g) Detection of cleavages in ss M13mp7 DNA: Agarose gel (1.4%) electrophoresis was used to detect cleavage of the ss circular DNA, as described by Been and Champoux, Methods in Enzymol. 101:90–98,1983. Single cuts convert the circles to linear DNA, which migrates more rapidly than the closed circles (FIG. 6; conversion from CF to LF). Digestion with EcoRI served as a control, since there is an EcoRI site in the hairpin formed by the invert repeat in M13mp7 DNA (FIG. 3).

EXAMPLE II

Example II describes the use of the enzyme-adapter complex to cleave ss DNA at a predetermined site.

(a) Digestion of M13mp7 ss circular DNA with the FokI restriction enzyme in presence of the left (32-mer) and right (34-mer) adapters: FIG. 6 illustrates electrophoretic separation of linear and circular forms of M13mp7 ss DNA carried out in horizontal 1.4% agarose gels in Tris-borate (Peacock) buffer for 3 h at 120 V, and generally following the procedure of Been and Champoux, M13mp7 ss circular DNA was prepared as described by Maniatis et al. (1982). Each lane contains 2 ug of this DNA (i) suspended in total volume of 20 ul of FokI buffer (20 mM KCl, 10 mM Tris. HCl, pH 7.5, 10 mM MgCl$_2$, b 0.5 mM DTT), (ii) digested or otherwise treated, (iii) precipitated with 4 vols. of 95% ethanol in presence of 0.3 M Na acetate, for 10 min. at −70° C., and centrifuged in microfuge for 10 min, (iv) washed with 70% ethanol and dried under vacuum, and resuspended in 20 ul of alkaline sample mix (30 mM NaOH, 2 mM EDTA, 7% Ficoll, 0.1% SDS, and 0.01% brom- phenol blue). DNA bands were stained with ethidium bromide (see FIG. 4).

Lane 1 (FIG. 6) contains untreated M13mp7 DNA [over 90% of circular form (CF), upper band, and less than 10% of linear form (LF), lower band] Lane 2 contains the same DNA treated with 12 units FokI/20 ul for 2 h at 37° C. in buffer (see above). Lanes 3 and 4 contain the same DNA hybridized with 15-fold molar excess of 32-mer and 34-mer adapter, respectively. Hybridization procedure consisted of 5 min. heating at 70° C. followed by 1 h at 37° C. in FokI buffer. There is no DNA cleavage in lanes 1–4, which represent negative controls. Lanes 5 and 6 represent the same treatment as in lanes 3 and 4 followed by FokI digestions as in lane 2. Here one sees specific cleavage of M13 ss DNA. Lane 7 represents, as a positive control, i.e., digestion with EcoRI (16 u/20 ul 1 h, 27° C.) in FokI buffer plus Tris.HCl to 100 mM (pH 7.5). Lanes 8 and 9 represent the same treatment as in lanes 5 and 6 followed by 1 h EcoRI digestion as in lane 7 which allows location of FokI adapter cut sites. Designations a+b+d and c refer to bands in lanes 5 and 6 of FIG. 6 and to the corresponding fragments in FIG. 3. For size markers see FIG. 7.

(a) As shown in FIG. 6 (lanes 1–4), neither FokI alone nor the adapters alone cleave circular M13mp7 DNA. However, when either the left or right adapter was first annealed to the ss DNA followed by addition of FokI, the circles were linearized with over 90% efficiency. Both adapters participate in the endonucleolytic reaction, but the right (34-nucleotide) adapter seems to be more efficient.

(b) Secondary cuts by the FokI-adapter combination: Careful examination of lanes 5 and 6 in FIG. 6 and lanes 2–6 in FIG. 7 shows two more bands in addition to the 7238-nucleotide band representing the entire linear ss DNA of M13mp7. The appearance of the two secondary bands seems to depend on the conditions of the reaction.

(c) Mapping of the cuts in M13mp7 DNA: To determine the positions of the primary and secondary cuts, M13mp7 ss DNA was cleaved with both the FokI-adapter complex and the reference EcoRI enzyme, which cuts within the M13mp7 hairpin as shown in FIG. 3. The results shown in lanes 8 and 9 (FIG. 6) appear to be consistent with the positions of the FokI cuts as shown in FIG. 3. Cleavages at site I are located within the 14-nucleotide target sequences (nucleotides 6938–6951; FIG. 2), and cleavage(s) at site II seems to occur at a perfect 9-nucleotide match (nucleotides 1340–1348) between the adapter and the M13 ss DNA as shown by nucleotide sequencing and indicated by the dots:

The upward arrow specifies the cut in the ss DNA directed by the 34-nucleotide adapter. Cleavage directed by the left 32-nucleotide adapter should be on the right edge of the 9-nucleotide homology (FIG. 2), consistent with the lower yield of secondary cuts (compare lanes 5 and 6, FIG. 6). (The last digits of the numbers match the corresponding nucleotides).

EXAMPLE III

Example III illustrates various conditions of the cleavage reaction.

(a) Cleavage with the preformed enzyme-adapter complex: In the procedure described in Example II, the adapter was annealed to M13mp7 DNA before addition of FokI. Here the enzyme was first saturated with the adapter and only then allowed to react with the target M13mp7 ss DNA.

Thus, when adapter is in excess, the free adapter molecules should bind to the M13 ss target DNA and interfere with cutting by the enzyme-adapter complexes. On the other hand, when enzyme is in excess, such competition should not occur since free enzyme does not recognize the ss target DNA.

Figure 7A:
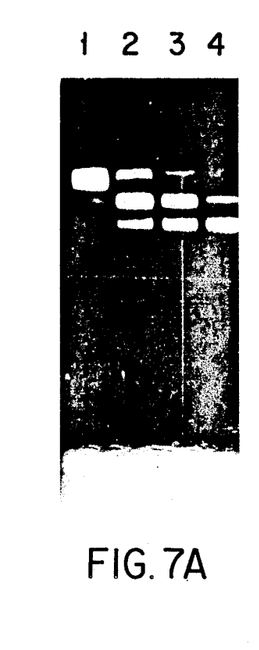
FIG. 7 illustrates photographs of gels of a preformed enzyme-adapter complex used to digest M13mp7. The effects of salt concentrations and annealing conditions between the adapter and target DNA are also shown.

Therefore, increasing concentrations of the FokI and a constant amount of adapter to preform the enzyme-adapter complexes were used as follows:

Lane 1 in FIG. 7A corresponds to the untreated M13 circular ss DNA control (as in lane 1, FIG. 6). For lanes 2–4, various amounts of FokI (12, 24, and 36 units, respectively) were combined with 34-mer (amount identical to that in FIG. 5; denatured for 5 min at 70° C.) and incubated for 10 min. at 37° C. in 20ul of FokI buffer. To each enzyme adapter preparation, 2 ug of M13mp17 circular ss DNA was added and the digestion carried for 1 h at 37° C. in the total volume of 30 ul. Other procedures were as in FIG. 6.

Figure 7B:
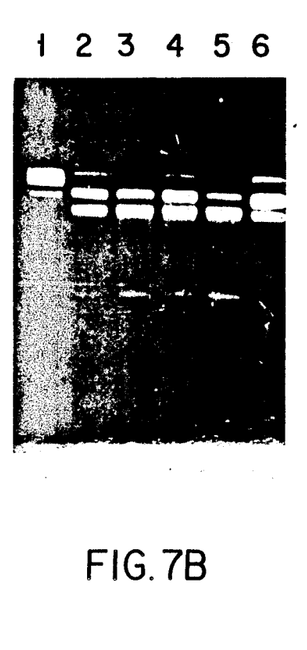

(b) Effect of buffer, KCl and Mg++ concentrations: Lanes 1 and 2 of FIG. 7B correspond to lanes 1 and 6 in FIG. 6. Lanes 3–6 correspond to the following variants of the experiment in lane 2: in lanes 3 and 4, the FokI buffer was diluted twofold and fourfold, respectively, both for hybridization and digestion. In lanes 5 and 6, all KCl was removed from the FokI buffer. Moreover, in lane 6 the Mg++ concentration was reduced fourfold (from 10 to 2.5 mM $MgCl_2$).

Figure 7C:
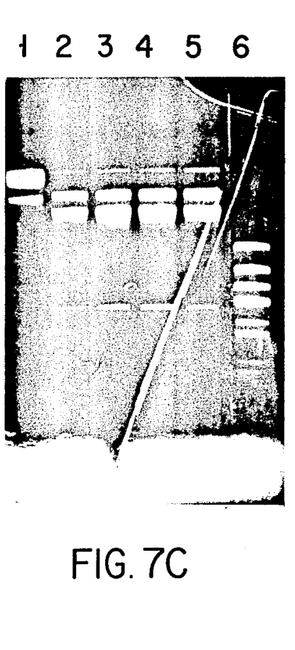

(c) Effect of the time period of the DNA-adapter hybridization: Lanes 1 and 2 of FIG. 7C correspond to lanes 1 and 2 in panel B. Lanes 3–5 correspond to lane 2, but the time of M13 ss DNA-adapter (34-mer) hybridization was reduced to 30, 15 and 5 min., respectively. Lane 6 (ss size standards) represents ss DNA fragments of the plasmid pRHP233 denatured and electrophoresed in the alkaline sample mix. The size of the fragments (from the top) are: 3636, 3097, 2459, 2443 nucleotides, followed by two doublets (complementary strands) of 1700 and 1159 nucleotides, respectively. Panels (A), (B), and (C) represent separate experiments run on different days.

As shown in FIG. 7A, such complexes do cleave M13 ss DNA, and as predicted above, the cleavage is more efficient at increasing FokI/adapter ratios (lanes 2–4). It also appears that use of the preformed enzyme-adapter complex has little effect on the proportion of the secondary cuts (cut II in FIG. 3).

All the reactions discussed in Examples II and III were carried out in buffer consisting of 20 mM KCl, 10 mM Tris-HCl, 10 mM $MgCl_2$ and 0.5 mM DTT. More stringent annealing conditions were explored, i.e., at decreasing salt concentrations, to determine whether the proportion of secondary cuts could be lowered, while cleavage efficiency remains substantially unaffected. As shown in FIG. 7B (lanes 3 and 4), twofold or fourfold dilution of the buffer still permits the reaction to proceed, while the ratio of the primary to secondary cuts seems to be slightly increased. Even total elimination of the KCl component results in the selective and efficient cleavage (lane 5). The most selective cleavage was obtained in the absence of KCl and 2.5 mM MgCl₂ (lane 6).

A standard time of 1 h annealing at 37° C. between adapter and target M13mp7 ss DNA was utilized before adding the enzyme. As shown in FIG. 7C, the annealing time could be reduced to 5 min. with hardly any change of the digestion pattern.

EXAMPLE IV

Figure 8:
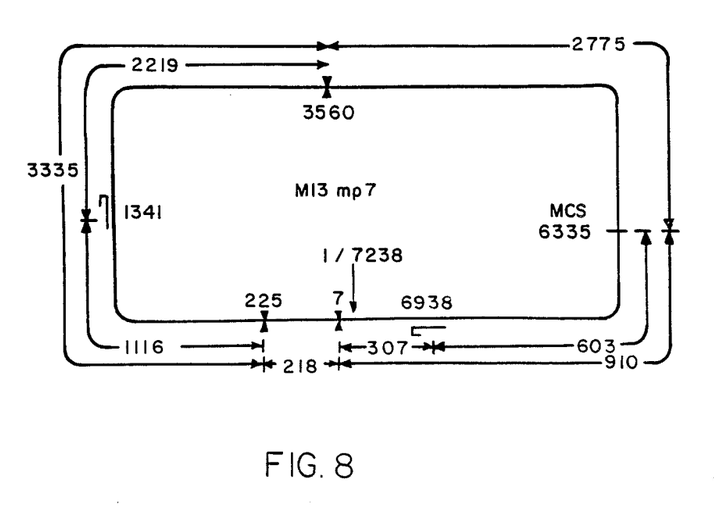
FIG. 8 shows a schematic representation of M13mp7 ds DNA.

Example IV describes preparation of double-stranded DNA fragments, using the enzyme-adapter complex. The adapter DNA comprising the 5' double-stranded hairpin domain and 3' ss domain (FIG. 1 and FIG. 2b) may be used as a primer for the synthesis of the complementary DNA strand. This adapter was annealed with the ss M13mp7 template, with adapter attaching at sites I and II (FIG. 3). Upon addition of PolIk (Klenow fragment of E. coli DNA polymerase I) and all four dNTP's, the DNA synthesis was carried out for 0.5–2 hrs at 20° C. in the FokI buffer. FokI enzyme was added either 5 min after initiation of complementary DNA synthesis or at the end of reactions. In both cases two new DNA fragments were produced, and are initiated and cut at site I (1341) and the other at site II (6938) (see FIGS. 3 and 8). The sizes of novel fragments were 1116 bp and 603 bp, because they were also cut at the regular sites at nucleotide 225 and 6335 (FIG. 8). Digestion of double-stranded RF form of M13mp7 DNA produced only four fragments, 3335, 2775, 910 and 218 bp long (FIG. 8). Thus, the 1116-bp and 603-bp fragments were novel and produced by the novel enzymatic activity of the adapter-FokI complex. The 1116-bp fragment was produced with high yield because there is a perfect match between the adapter and M13mp7 as DNA at site I (nucleotide 1341). The yield of the 603-bp fragment was lower because only 9 out of 14 nucleotides of adapter did pair at site II (FIGS. 3 and 8); however, PolIk was able to use this primer with only 9 bp match, even though the 3'-terminal nucleotide of the adapter was not paired. The resulting novel DNA fragments (with blunt ends due to the PolIk reaction) were blunt-end cloned into M13mp17 vector and their ends were sequenced. In general, the sequences matched the predicted sequences of the novel ends. This method of preparing double-stranded DNA fragments with one predetermined terminus appears to be both simple and reliable. The second terminus of the fragment could be either at FokI site (FIG. 8), or any other end generated by another restriction enzyme of choice.

What is claimed is:

1. A universal restriction endonuclease composition which cleaves a target DNA at a predetermined site comprising:
   (a) an oligonucleotide adapter which comprises a double-stranded nucleotide sequence corresponding to the recognition site of the restriction endonuclease and a single-stranded nucleotide sequence complementary to the predetermined site of the target DNA: and
   (b) a restriction endonuclease;
   wherein the oligodeoxynucleotide adapter is designed to mimic the relationship which exists between the recognition site and cleavage site of the restriction endonuclease.

2. The universal restriction endonuclease composition of claim 1, wherein the oligodeoxynucleotide adapter and restriction endonuclease are covalently bound.

3. The universal restriction endonuclease composition of claim 1, wherein the restriction endonuclease is a Class II enzyme selected from the group consisting of BbvI, BbvII, BinI, FokI, HgaI, HphI, MboII, MnlI, SfaNI, TaqII, and Tth111II.

4. The universal restriction endonuclease composition of claim 3, wherein the restriction endonuclease is FokI.

5. The universal restriction endonuclease composition of claim 1, wherein the restriction endonuclease is a Class III enzyme selected from the group consisting of EcoP1, EcoP15, HineI, and HinfIII.

6. A method for cleaving a target DNA at a predetermined site comprising contacting the target DNA in an appropriate buffer solution with a universal restriction endonuclease composition in an amount and for a time sufficient to cause the desired cleavage to occur, said universal restriction endonuclease composition comprising:
   (a) an oligonucleotide adapter which comprises a double-stranded nucleotide sequence corresponding to the recognition site of the restriction endonuclease and a single-stranded nucleotide sequence complementary to the predetermined site of the target DNA; and
   (b) a restriction endonuclease;
   wherein the oligodeoxynucleotide adapter is designed to mimic the relationship which exists between the recognition site and cleavage site of the restriction endonuclease.

7. The method of claim 6, wherein the oligonucleotide adapter and restriction endonuclease are covalently bound.

8. The method of claim 6, wherein the contacting of the universal restriction endonuclease composition with the target DNA comprises:
   (a) complexing the oligodeoxynucleotide adapter to the predetermined site of the target DNA; and
   (b) adding the appropriate restriction endonuclease to the DNA-adapter complex.

9. The method of claim 8, wherein the target DNA is single stranded.

10. The method of claim 9, comprising the further step of extending the 3'-OH terminus of the oligodeoxynucleotide adapter along the single-stranded target DNA to form a double-stranded DNA containing the predetermined cut site prior to addition of the appropriate restriction endonuclease.

11. The method of claim 6, wherein the oligodeoxynucleotide adapter is complexed with the restriction endonuclease and contacting comprises complexing the complex with the target DNA.

12. The method of claim 11 wherein the target DNA is single-stranded.

* * * * *